Figure 1:
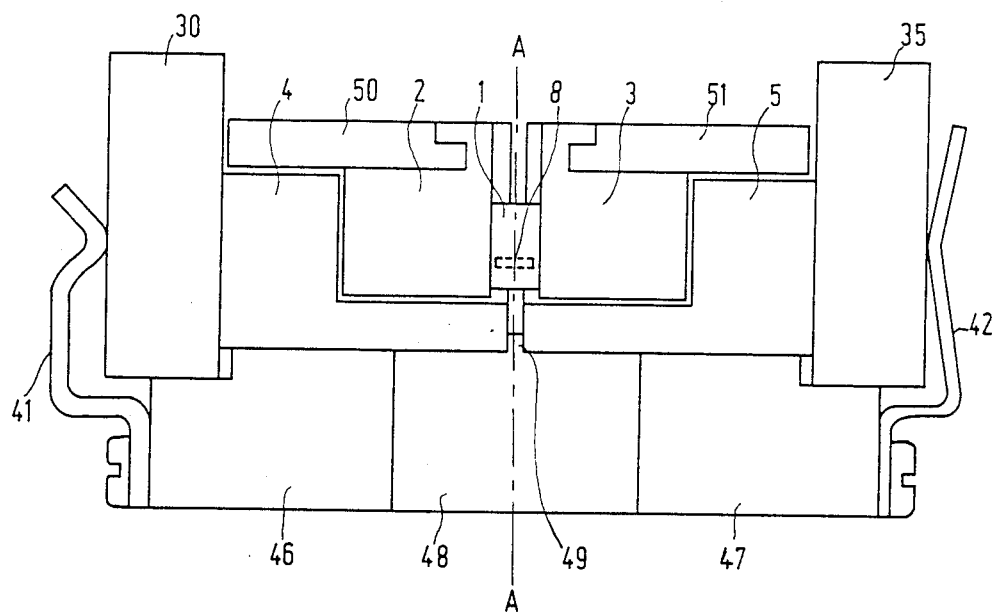

United States Patent [19]

Churchill et al.

[11] Patent Number: 4,729,656
[45] Date of Patent: Mar. 8, 1988

[54] ELECTROTHERMAL ATOMISER

[75] Inventors: John E. Churchill; Michael D. Flack; David S. Widmer, all of Cambridge, England

[73] Assignee: U.S. Philips Corporation, New York, N.Y.

[21] Appl. No.: 28,003

[22] Filed: Mar. 19, 1987

Related U.S. Application Data

[63] Continuation of Ser. No. 741,988, Jun. 6, 1985, abandoned.

[30] Foreign Application Priority Data

Jun. 11, 1984 [GB] United Kingdom ............... 8414815

[51] Int. Cl.$^4$ .......................................... G01N 21/74
[52] U.S. Cl. ...................................... 356/312; 356/244
[58] Field of Search ................................. 356/244, 312

[56] References Cited

U.S. PATENT DOCUMENTS

| | | | |
|---|---|---|---|
| 3,895,873 | 7/1975 | Dennison et al. ............... | 356/244 X |
| 3,982,834 | 9/1976 | Tamm ............................... | 356/312 |
| 4,176,956 | 12/1979 | Tomoff et al. .................. | 356/244 X |
| 4,225,234 | 9/1980 | Schmider et al. ............... | 356/312 |

Primary Examiner—Vincent P. McGraw
Attorney, Agent, or Firm—Paul R. Miller

[57] ABSTRACT

An electrothermal atomizer comprises a tubular graphite body (1) whose ends are clamped between two pairs of graphite contact members (2,4;3,5) which are arranged to form a containment zone for the tubular body (1). The graphite contact members (2,4;3,5) clamp the ends of the tubular body (1) in a radial direction and are separable from each other by an upwardly pivoting movement of the members (2,3). The lower contact members (4,5) are urged towards each other in the direction of the longitudinal axis of the tubular body (1) by means of a leaf spring (42) so that when the clamping force on the tubular body (1) is released by raising the upper contact members (2,3) the tubular body (1) is lightly retained by the lower contact members (4,5). Thus easy access for adjusting the orientation of the tubular body (1) can be obtained, for example to adjust the orientation of the dosing aperture and/or probe entry slot (8).

7 Claims, 8 Drawing Figures

ELECTROTHERMAL ATOMISER

This is a continuation of application Ser. No. 741,988, filed June 6, 1985, now abandoned.

The invention relates to an electrothermal atomiser for atomic spectroscopy comprising a tubular graphite body, first electrical contact means for connecting an electrical current supply to one end of the tubular body with the first electrical contact means comprising a first graphite member and second electrical contact means for connecting an electrical current supply to the other end of the tubular body with the second electrical contact means comprising a second graphite member.

Such an electrothermal atomiser is disclosed in U.K. Patent No. 1461807 and in an article entitled "Advances in Graphite Furnace Atomisation" by M. W. Routh, P. S. Doidge, J. Chidzey, and B. Frary which was published in the May 1982 issue of International Laboratory. The atomisers disclosed in both these publications have graphite contact members which provide electrical contact means to a graphite tubular body and the tubular body is enclosed within a containment zone which is separable in a direction parallel to the longitudinal axis of the tubular body to allow removal and replacement of the tubular body. In both atomisers the graphite contact members have a circular cross-section and are force fitted into an aperture in a copper electrode for connection to an electrical power supply. The graphite contact members require periodic replacement and a special tool is required to force the contact member into the aperture in the copper electrodes to ensure a reasonable electrical connection. Further access to the tubular body to align the dosing aperture is difficult since the tubular body is located only when the contact members are brought into contact with its ends and in that circumstance the tubular body is shrouded by the walls of the containment zone.

It is an object of the invention to enable the provision of an electrothermal atomiser in which the effect of one or more of the disadvantages of the atomisers disclosed in the publications mentioned in the preceding paragraph is mitigated.

The invention provides an electrothermal atomiser as set forth in the opening paragraph characterised in that the first and second graphite members surround a major portion of the tubular body to form a containment zone for protective gas flowing over the tubular body, that the first and second graphite members each comprise first and second separable parts, that the first and second graphite members are separate in a direction transverse to a plane which is parallel to the longitudinal axis of the tubular body, and that the first and second graphite members are so arranged that, when the two parts are separated, the tubular body can be located between and supported by the first separable part of the first and second graphite members.

By using the inventive idea an atomiser can be constructed in which the graphite tubular body can be readily removed and replaced and in which alignment of the tubular body within the atomiser may be readily achieved.

The first separable part may contain a groove for locating the end region of the tubular body with the groove forming an electrical contact area between the tubular body and the contact member. This arrangement provides a positive locating means for the tubular body and enables a good electrical connection between the tubular body and the contact member to be achieved.

The second part of the first and second contact members may be pivotally separable from the first part. This enables the production of a convenient mechanical construction in which an easy access to the tubular body may be provided.

The first parts of the first and second contact members may be urged towards each other in the direction of the longitudinal axis of the tubular body by means of a spring. Thus the tubular body can be gripped between the first parts of the contact members regardless of the orientation of these parts. A further function of this urging together of the first parts in the embodiment described is to seal the ends of the tubular body against protective gas supply inlet means.

The longitudinal axis of the tubular body may extend horizontally and the first and second parts of the contact members may have mating surfaces which are upwardly inclined from the front of the atomiser. The inclined mating surface improves still further the access to the tubular body when the two parts are separated and the horizontal mounting of the tubular body allows it to be retained on the first parts of the contact members even in the absence of means urging the first parts together.

The first and second graphite contact members may have a flat planar surface for mating with metallic conductors. This enables a good electrical connection to be made without requiring large contact forces. Thus the graphite members may be loosely coupled to the metallic conductors with the clamping forces being applied when the two parts of the contact members are mated. This enables a construction to be achieved in which replacement of the graphite contact members can be simply performed without requiring the use of special tools.

Both parts of the graphite contact members may be arranged to be connected to an electrical supply. This enables an even current distribution over the wall of the tubular body to be achieved.

Figure 2:
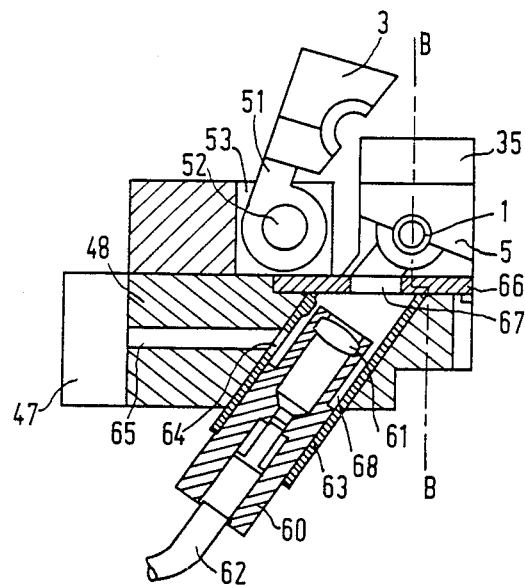
Figure 3:
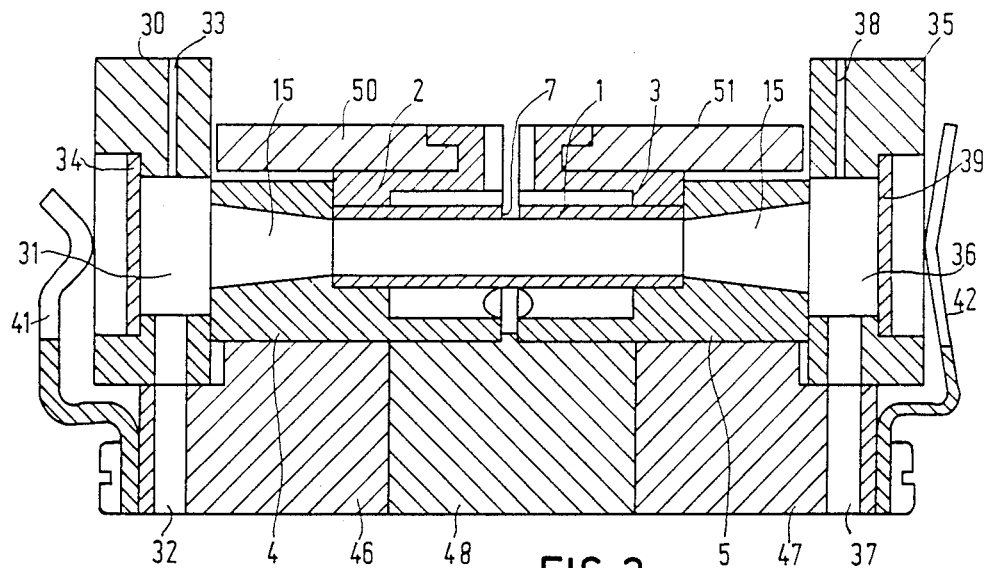
Figure 4:
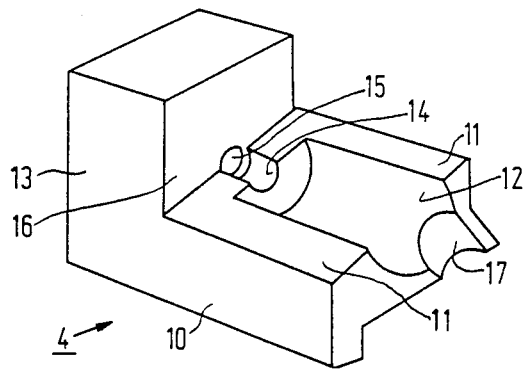
Figure 5:
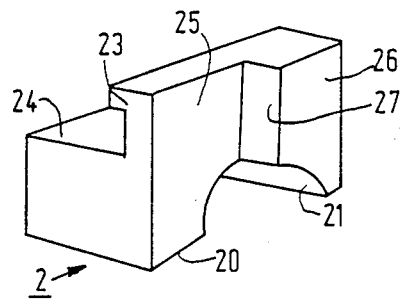
Figure 6:
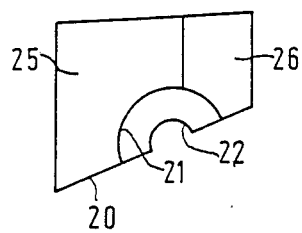
Figure 7:
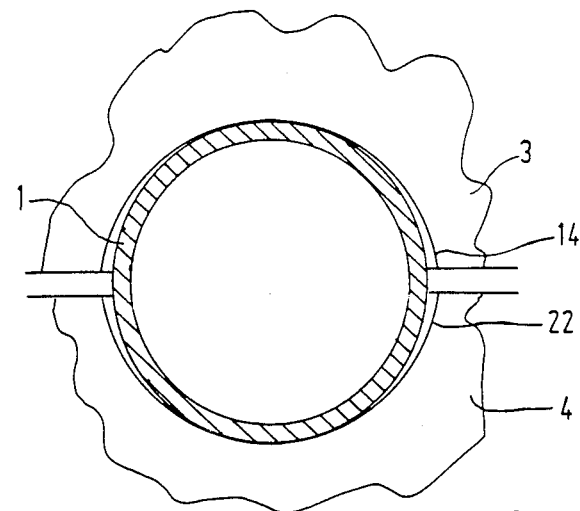
Figure 8:
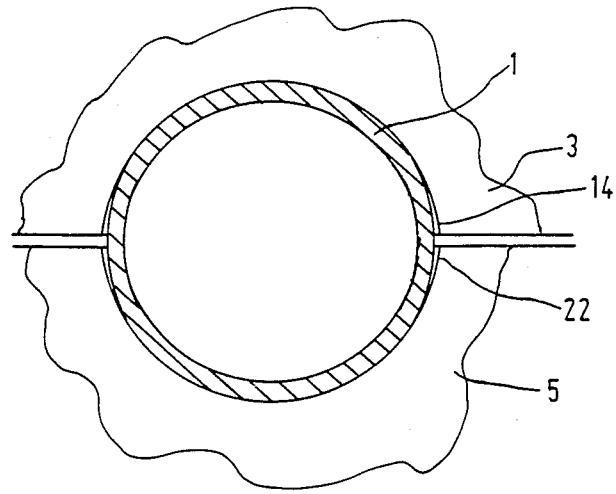

An embodiment of the invention will now be described, by way of example, with reference to the accompanying drawings, in which:

FIG. 1 shows a front elevation of an electrothermal atomiser according to the invention, FIG. 2 is a cross-sectional view on line A—A of FIG. 1 with the upper graphite contact member pivotted upwardly away from the lower graphite contact member, FIG. 3 is a cross-sectional view on line B—B of FIG. 2 with the upper and lower graphite contact members clamped together, FIG. 4 is a perspective view of the lower graphite contact member, FIG. 5 is a perspective view of the upper graphite contact member, FIG. 6 is an end elevation of the upper graphite contact member, and FIGS. 7 and 8 illustrate the interation between the upper and lower graphite contact members and the graphite tubular member.

FIGS. 1, 2 and 3 show an electrothermal atomiser according to the invention which comprises a graphite tube 1 which, in operation, is clamped at each end between upper 2,3 and lower 4,5 graphite contact members which also provide an enclosure to contain a protective gas atmosphere when the tube 1 is to be heated to high temperatures. The enclosure is not completely sealed as access is required to the tube 1 for inserting a sample into the tube via a dosing aperture 7 and also possibly to a slot 8 for entry of a probe through the wall of the tube 1, which entry may be achieved as described in U.K. Patent Application No. 8305745 corresponding to U.S. patent application Ser. No. 581,484, filed Feb. 17, 1984, and assigned to the same assignee as the present application.

FIGS. 4, 5 and 6 show the form of the graphite contact members 2 and 4 with the members 3 and 5 being of substantially the same form but of the opposite hand. The graphite member 4 shown in a perspective view in FIG. 4 is substantially L-shaped with the horizontal limb 10 having an inclined upper surface 11 in which is formed a semi-circular groove 12. The groove 12 extends from the free end of the limb 10 towards the other limb 13 of the member 4 but stops short of the junction of the two limbs. A semi-circular groove 14 which has a smaller radius than that of the groove 12 forms an extension of the groove 12 and extends to the other limb 13 of the member 4. The radius of the groove 14 is chosen to provide good electrical contact between the graphite member 4 and the end of the graphite tube 1, while the radius of the groove 12 is chosen to provide electrical isolation and to enable easy removal and replacement of the tube 1. The length of the groove 14 is chosen to provide the required contact surface area for efficient conduction of electrical current into the tube 1. An aperture 15 is formed in the limb 13 which aperture has a diameter substantially equal to the internal diameter of the tube 1 at the surface 15 of the limb 13 and extends through the limb 13 in the form of a truncated cone with the minimum diameter at the surface 16. A further semi-circular groove 17 extends radially into the groove 12 adjacent to the free end of the limb 10.

A perspective view of the graphite contact member 2 is shown in FIG. 5 and an end elevation is shown in FIG. 6. The member 2 comprises a rectangular block having an inclined lower face 20 in which a semi-circular groove 21 is formed formed with the groove 21 having the same length and diameter as the groove 12 in the member 2. A further semi-circular groove 22 having the same length and diameter as the groove 14 in the member 4 is formed between the end of the groove 12 and the hidden face of the member 2. An inverted L-shaped portion 23 extends from the upper surface 24 of the member 2. The groove 21 extends from an end which comprises two parallel faces 25, 26 separated by a step 27.

Returning to FIGS. 1 to 3, the graphite contact members 4 and 5 are mounted on copper electrodes 46 and 47 which are separated by a block 48 of electrically insulating material having an upstanding rib 49 to prevent the graphite members 4 and 5 making electrical contact with each other. A clearance gap between the rib 49 and the graphite members 46 and 47 normally exists when the tubular body 1 is inserted between the members 46 and 47 to ensure that sealing of the ends of the body 1 onto the members 46 and 47 can occur. The upper surfaces of the copper electrodes 46 and 47 are a ground finish and are maintained in the same plane to the best tolerance obtainable commercially to ensure the best possible electrical contact. The graphite contact members 4 and 5 together with the members 2 and 3 cover the copper electrodes to protect them from corrosive products from the sample, provide a seating and good electrical contact between the graphite tube 1 and the electrodes 46 and 47, and provide a means for introducing protective gas into the interior of the graphite tube 1.

A first gas entry block 30 is lightly sealed against the graphite contact member 4 and comprises a chamber 31 which is open to the aperture 15 in the graphite contact member 4 and which is provided with a gas inlet aperture 32, a bleed hole 33 and a quartz window 34. A second gas entry block 35 is lightly sealed against the graphite contact member 5 and comprises a chamber 36 which is open to the aperture 15 in the graphite contact member 5 and which is provided with a gas inlet aperture 37, a bleed hole 38 and a quartz window 39.

Thus an optical path is provided from the quartz window 34 via the chamber 31, aperture 15 in graphite contact member 4, the interior of the graphite tubular member 1, aperture 15 in graphite contact member 5, and chamber 36 to the quartz window 39. Further when the protective gas flow is stopped a volume is formed which has outlets via the bleed holes 33 and 38 and via the central dosing aperture 7 in the tubular member 1. The aperture 7 is that normally provided for inserting a sample to be atomised into the tubular member 1. If the sample is to be introduced into the tubular member 1 on a probe there may also be a further aperture (in the form of a longitudinally extending slot 8) in the tubular member 1.

The assembly of the gas entry blocks 30, 35, graphite contact members 4, 5 and graphite tubular member is located between a stop 41 mounted on the electrode 46 and a leaf spring 42 mounted on the electrode 47. The electrodes 46 and 47 and insulating block 48 are bolted together to form a rigid assembly.

As can be seen from FIG. 2 which is a cross-section on line A—A of FIG. 1 the upper graphite contact members 2, 3 are carried by copper bars 50, 51 whose other ends are pivotted on a shaft 52 mounted on end members, one of which is shown referenced 53. The upper graphite contact member 3 is shown in its raised position in FIG. 2, in which position the graphite tubular member 1 is accessible for removal or replacement. The insulating block 48 carries a temperature sensing arrangement for measuring the temperature of the tubular member 1. The temperature sensing arrangement comprises a tubular member 60 in which a lens 61 is mounted with the lens 61 focussing radiation emitted by the tubular member 1 onto the end of an optical fiber 62. The other end of the optical fiber 62 illuminates an optical pyrometer to measure the temperature of the tubular member 1. The tubular member 60 is mounted within a further tubular member 63 in the insulating block 48 the further tubular member 63 being open at both ends and having an aperture 64 in its wall, the aperture 64 communicating with a passageway 65 in the insulating block 48. A plate 66 of ceramic material is inset into the block 48 under the graphite contact members 4 and 5 so that the material of the insulating block 48 is shielded from the high temperatures reached by the tubular member 1. The ceramic plate 66 has an aperture 67 which is aligned with the grooves 17 in the graphite contact members 4,5 to enable radiation from the tubular member 1 to pass to the lens 61. Protective gas is fed via the passageway 65 and aperture 64 to an annular chamber 68 formed between the tubular members 60 and 63 and subsequently over the lens 61 and through the aperture 67 along a channel formed by the grooves 17 in the graphite contact members 4 and 5 and round the outside of the graphite tubular member 1.

In operation a sample is deposited into the tubular member 1 through the dosing aperture 7. The temperature of the tubular member 1 is then raised to dry the sample and possibly raised still further to ash the sample depending on the composition of the sample. The drying and ashing stages may be carried out with either a flow of air or of protective gas through inlet apertures 32 and 37 and passageway 65 depending on the nature of the sample. In all cases before the temperature of the tubular body 1 is raised to the atomisation temperature a flow of protective gas is produced so that the tubular body contains and is surrounded by a protective gas. It is usual to stop the gas flow to the interior of the tubular body 1 during the atomisation phase. It has been found that if the bleed holes 33 and 38 are not present in the atomiser shown the measured chemical sensitivity is reduced. It is believed that the explanation for this phenomenon is that when the temperature of the tubular member 1 is rapidly increased the gas contained in the volume formed by the chambers 31,36, apertures 15 and the tubular body 1 expands and is forced out of the dosing aperture 7 carrying with it part of the sample. By providing an alternative escape path for the expanding gases by means of the bleed holes 33 and 38 the escape of the expanding protective gas through the dosing aperture may be substantially reduced with a corresponding reduction in the loss of sample. With the bleed holes having a diameter substantially equal to that of the dosing aperture a doubling of sensitivity has been achieved. Clearly as the diameter of the bleed holes is increased so the proportion of the gases escaping through the dosing aperture is decreased. However, there is a limit to the diameter of the bleed holes since it is possible to fill the interior of the tubular body 1, and it is also desirable to have some scavenging action to carry away components produced during the ashing phase.

With the atomiser described access to the tubular graphite member 1 is facilitated by the horizontal split between the graphite contact members 2 and 4 and 3 and 5 since when the upper members 2 and 3 are pivotted upwardly the graphite tubular member 1 is retained between the faces 16 of the lower members 4 and 5 in the grooves 14. The tubular member 1 may then be easily removed and replaced and the orientation of the dosing aperture 77 and probe entry aperture, if provided, adjusted. The light pressure on the ends of the tubular member 1 caused by the leaf spring 42 may be mechanically relieved before removal of the tubular member if desired. This arrangement also has the advantage that the graphite contact members 4 and 5 may be easily removable since when the members 2 and 3 are pivotted upwardly no pressure is applied to the contact members 4 and 5. In practice the members 4 and 5 may be loosely fitted on the electrodes 46 and 47, for example by means of spring clips, and the clamping force produced by the lowering of the upper graphite contact members 2 and 3 being sufficient to produce a good electrical connection.

FIGS. 7 and 8 illustrate how electrical contact between the ends of the tubular member 1 and the graphite contact members 2 and 4 and 3 and 5 is obtained. Each end of the tubular member 1 is located between respective upper and lower graphite contact members 2,4 and 3,5. The upper and lower graphite members are clamped together with a force which is sufficient to flex the ends of the tubular body 1 so that its external surface conforms to the internal surface of the grooves 14 and 22 in the graphite contact members. This is illustrated in FIGS. 7 and 8 where the cross-section of the tubular member 1 is shown before and after application of clamping force, respectively. It can be seen from FIG. 8 that after application of the clamping force the area of the tubular member 1 in contact with the graphite contact members has been substantially increased thus giving a better electrical connection. The tubular member 1 is normally made from graphite as this material has the necessary chemical and physical properties but the use of other materials, for example the refractory metals, is possible in some circumstances. Typical dimensions for the tubular member 1 when made from electrographite are 5 mm bore with 600 $\mu$m wall thickness. When made totally from pyrolytic graphite the wall thickness may be reduced to about 300 $\mu$m. These dimensions are purely exemplary and may be changed, for example when using probe sampling. It has been found convenient to make the external diameter of the tubular member 1 and the diameter of the grooves 14 and 22 such that a tubular member at the high end of the manufacturing tolerance has a diameter equal to the diameter of a groove 14,22 at the low end of its manufacturing tolerance. A clamping force of from 4 to 5 Kg between the graphite contact members at each end, i.e. a total clamping force of 8 to 10 Kg on the tubular member, has been found to produce a good electrical connection for tubular members having the dimensions given herein when the contact area extends over a 2 mm length of the tube.

In order to produce a desired clamping force between the graphite contact members 2 and 4 and 3 and 5 a mechanism which either pulls down the copper bars 50,51 from underneath or pushes down the copper bars from on top is required. The design of such mechanisms is well known to those skilled in the art.

We claim:
1. An electrothermal atomizer for atomic spectroscopy comprising
   a tubular graphite body,
   first electrical contact means for connecting an electrical current supply to one end of said tubular body, said first electrical contact means including a first graphite member, and
   second electrical contact means for connecting an electrical current supply to the other end of said tubular body, said second electrical contact means including a second graphite member,
   the improvement comprising
   said first and second graphite members forming an enclosure surrounding a major portion of said tubular body to provide a containment zone for flowing protective gases over said tubular body, said first and second graphite members being slightly separated from one another to provide access to said tubular body,
   each of said first and said second graphite members including first and second separable portions surrounding said tubular body, said first and said second graphite members being arranged such that said tubular body is supported by said first portions of each of said first and said second graphite members upon separating said second separable portions from said first portions, and
   said first and said second separable portions being separated from one another in a direction transverse to a plane parallel the longitudinal axis of said tubular body.

2. An electrothermal atomizer according to claim 1, wherein each of said first separable portions contains a groove for locating a respective end region of said tubular body, each of said grooves forming an electrical contact area between said tubular body and said first and second electrical contact means.

3. An electrothermal atomizer according to claim 1 or claim 2, wherein said second separable portions are fixed to a shaft to be pivotally separable from said first portions, said shaft being parallel to said longitudinal axis.

4. An electrothermal atomizer according to claim 3, wherein said first separable portions of each of said first and second graphite members are urged toward each other in a direction parallel to said longitudinal axis of said tubular body, said first separable portions being urged toward each other by a spring.

5. An electrothermal atomizer according to claim 3, wherein said longitudinal axis of said tubular body extends horizontally, and wherein said first and second separable portions have upwardly inclined mating surfaces.

6. An electrothermal atomizer according to claim 3, wherein said first and second graphite members have a float planar surface mating with a metallic conductor.

7. An electrothermal atomizer according to claim 3, wherein said first and second separable portions of each of said first and second electrical contact means are both connected to said electrical current supply.

* * * * *